United States Patent [19]

Yamashoji et al.

[11] Patent Number: 5,093,238

[45] Date of Patent: Mar. 3, 1992

[54] CHEMILUMINESCENT ASSAY FOR THE DETERMINATION OF DENSITY OF ACTIVITY OF VIABLE CELLS

[75] Inventors: Shiro Yamashoji; Kumiko Yamashoji; Tatsuhiko Ikeda, all of Kobe, Japan

[73] Assignee: Kings Brewery Co., Ltd., Hyogo, Japan

[21] Appl. No.: 407,354

[22] Filed: Sep. 14, 1989

[30] Foreign Application Priority Data

Dec. 16, 1987 [JP] Japan .................. 62-319677

[51] Int. Cl.$^5$ .......................... C12Q 1/02
[52] U.S. Cl. .......................... 435/29; 435/4; 435/25; 435/34; 436/172
[58] Field of Search ............ 435/4, 25, 29, 34, 904; 436/43, 172, 546, 800; 422/51, 52

[56] References Cited

U.S. PATENT DOCUMENTS

| | | | |
|---|---|---|---|
| 4,366,241 | 12/1982 | Tom et al. | 435/7 |
| 4,647,532 | 3/1987 | Watanabe et al. | 435/28 |
| 4,655,969 | 4/1987 | Richter et al. | 252/700 |
| 4,746,607 | 5/1988 | Mura et al. | 435/29 |
| 4,959,182 | 9/1990 | Schaap | 435/19 |

OTHER PUBLICATIONS

Mosmann, T., Journal of Immunological Methods 65:55–63 (1983), "Rapid Colorimetric Assay for Cellular Growth and Survival: Application to Proliferation and Cytotoxicity Assays".

DeLuca, M. and McElroy, W. D., Methods in Enzymology, vol. 57, pp. 3–15 (1978), "Purification and Properties of Firefly Luciferase".

Hastings-Methods in Enzymology, vol. 57 (1978) pp. 125–135.

Yamashoji et al.-Analytical Biochemistry, vol. 181 (1989) pp. 001 to 004.

*Primary Examiner*—Sam Rosen
*Attorney, Agent, or Firm*—Bryan, Cave, McPheeters & McRoberts

[57] ABSTRACT

A chemiluminescent assay for the determination of density or activity of viable cells which comprises incubating viable cells in the presence of a quinone whose reduced form redcues dissolved oxygen resulting in formation of hydrogen peroxide, reacting the hydrogen peroxide with a chemiluminescence reagent in the presence of a fluorescent substance to cause fluorescence and determining density or activity of the cells on the basis of the intensity of fluorescence.

5 Claims, 3 Drawing Sheets

CHEMILUMINESCENT ASSAY FOR THE DETERMINATION OF DENSITY OF ACTIVITY OF VIABLE CELLS

BACKGROUND OF THE INVENTION

1. Field of the Invention

This invention relates to a chemiluminescent assay for the determination of density or activity of intact viable (living) cells per se or of such cells in living tissue or organ for biological studies, which is convenient and exact.

2. Description of the Prior Art

The measurement of the growth rate of microorganisms, mammalian cells, and plant tissues is an important procedure in many biological assays. The viable cells can be measured by several staining methods which require several steps depending on the type of cells, but the staining methods are not useful for determining the activity of viable cells.

Recently, a colorimetric assay for cellular growth and survival using tetrazolium salt has been reported and is useful for measuring the activity of viable cells, in which MTT[3-(4,5-dimethylthiazol-2-yl)-2,5-diphenyl tetrazolium bromine] used for this assay is incorporated in viable cells, and a colored product is produced by active mitochondria (Mosmann, T. (1983) J. Immunol. Methods Vol. 65, pp. 55-63.

However, this procedure requires long incubation times. For example, mammalian cells are incubated with MTT for 4 hours at 37° C., and the formazan produced must be solubilized by the addition of an acid solution to minimize the interference of phenol red contained in normal tissue culture medium.

On the other hand, a bioluminescent assay is used to determine the intracellular concentration of NAD(P)H or ATP(Hasting, J. W. (1978) in Methods in Enzymology (Colowick, S, P., and Kaplan, N. O., Eds.), Vol. 57, pp. 125-134, Academic Press, Orlando, Fla.; De Luca, M., and McElroy, W. D. (1978) in Methods in Enzymology (Colowick, S, P., and Kaplan, N. O., Eds.), Vol. 57, p. 3, Academic Press, Orlando, Fla.). The procedure requires the extraction of NAD(P)H of ATP from the cells, and all instruments must be carefully washed to avoid the contamination of NAD(P)H or ATP. The luciferase used for this assay is expensive and furthermore is unstable.

SUMMARY OF THE INVENTION

Thus, the main object of the present invention is to provide a convenient and exact assay for the measurement of numbers and activities of viable cells, which are present in the form of intact cells or of an aggregative state such as in tissues or organs.

According to the present invention, there is provided a chemiluminescent assay for the determination of density or activity of viable cells which comprises incubating viable cells in the presence of an oxidized type quinone to produce hydrogen peroxide, reacting the hydrogen peroxide with an chemiluminescence reagent in the presence of a fluorescent substance to cause fluorescence and determining the density or activity of the cells on the basis of the intensity of fluorescence.

PREFERRED EMBODIMENTS OF THE INVENTION

(Gist and Principle of Assay)

Figure 2:
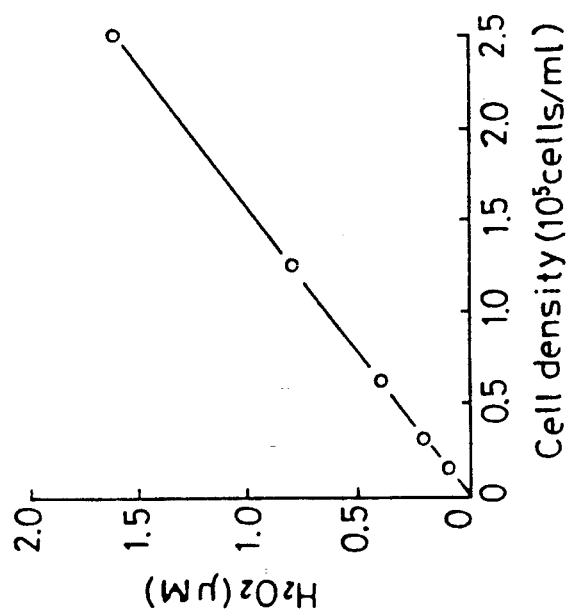
FIG. 2 shows a plot of $H_2O_2$ production vs. yeast cell density. The reaction mixture contained 20 mM imidazolenitrate buffer (pH 7.0), 0.5 mM menadione and yeast cells, and was kept at 34° C. for 2 minutes.

The chemiluminescent assay of the present invention is to incubate viable cells with an oxidized type quinone and then to assay $H_2O_2$ thus produced by a chemiluminescence reaction. Namely, It is considered that a cellular membrane contains a certain local redox enzyme which catalyzes the reduction of an extracellular oxidant by the aid of such intracellular reductant as nicotinamide adenine dinucleotide (NADH) and its phosphate (NADPH). Therefore, if an extracellular redox mediator such as quinone is reduced by the redox enzyme, said quinone will reduce dissolved oxygen to $H_2O_2$.

Now, we have found that the production of $H_2O_2$ promoted by said quinone, which is a carrier of hydrogen, is sharply correlated with the amount of intracellular NAD(P)H. The concentration (amount) of $H_2O_2$ produced is determined by the measurement of chemiluminescence which is generated in the mixture of $H_2O_2$, a fluorescent substance and an chemiluminescence reagent. This principle will become clearer by the following illustration.

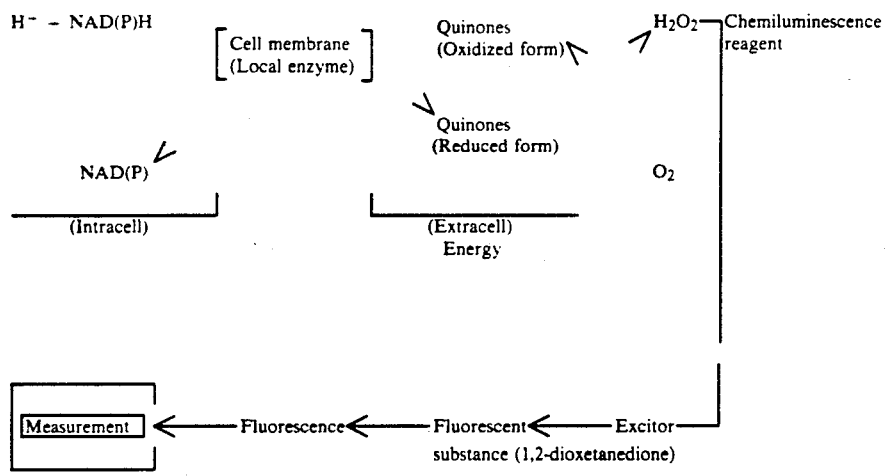

As seen from the above illustration, quinone is circulatorily changed from the oxidized form to reduced form and act as a catalyst for $H_2O_2$ production.

(Mechanism of Fluorescent Reaction)

According to the assay of this invention, the $H_2O_2$ formed will react with an aryl oxalate as a chemiluminescence reagent to yield 1,2-dioxetandione. 1,2-Dioxetandione will raise an energy level of a $\pi$ electron rich fluorescent substance such as pyrene, thereby causing fluorescence. The scheme of this reaction, when diphenyl oxalate and pyrene are used as an chemiluminescence reagent and a fluorescent reagent, can be summarized as follows;

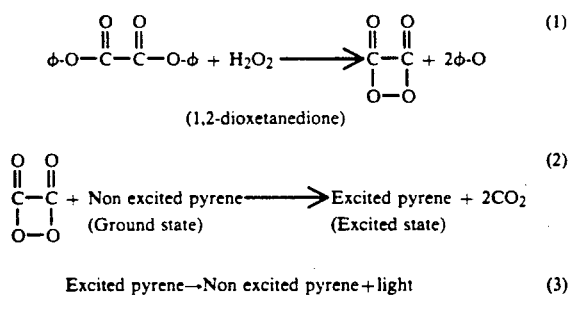

(In the above formula, $\phi$ shows phenyl radical.)

(Accuracy of the Measurement and Necessary Reaction Time)

According to the above fluorescent reaction, $H_2O_2$ is detectable at a concentration of $10^{-7}-10^{-3}$ mole/l. The reaction time is about 10 seconds. On the other hand, the incubation time required for generation of $H_2O_2$ depends on the physiological condition of cells. For example, yeast cells (10 μg/ml) produce a detectable amount of $H_2O_2$ within 30 seconds. Therefore, about 40 seconds are the minimum necessary time for the determination of the viable cell number and activity of yeast cells.

(Application)

As is clear by the above explanation, the chemiluminescent assay according to this invention can be applied to the measurement of the growth rate of cells having plasma membrane redox enzymes such as yeast cells, animal cells and plant cells. This assay is further applicable to animal and plant tissue. For example, plant roots will form $H_2O_2$ when the roots are soaked into a neutral solution containing a quinone. By determining the amount of $H_2O_2$ thus formed, the activity of the root can be assayed.

(Quinones)

Examples of the usable quinones include quinone derivatives such as benzoquinone, naphthoquinone, diphenoquinone and anthraquinone. However, it is preferable to use quinones which include an easily oxidizable moiety in addition to two oxo groups. The most preferred quinone is menadione (2-methyl-1,4-naphthoquinone), which is a physiological substance known as vitamin $K_3$.

(Chemiluminescence Reagent, and Fluorescent Substance)

Examples of the chemiluminescence reagent which can react with hydrogen peroxide are bis(2,4dinitrophenyl)oxalate (DNPO) and bis(2,4,6-trichloro-phenyl) oxalate (TCPO).

Also, excited intermediates, such as 1,2-dioxetane, 1,2-dioxetanone and 1,2-dioxetanedione are usable.

Examples of fluorescent substances useable with the present invention, include all fluorescent substances, but the most preferred substances are aromatic compounds having $\pi$-electrons such as pyrene and perylene in views of stability, cost and fluorescent intensity.

Figure 6:
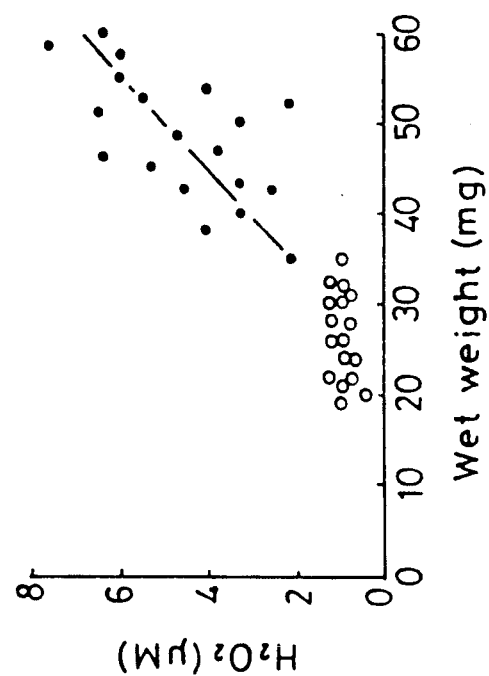
FIG. 6 shows a plot of $H_2O_2$ production vs. fresh wet weight of radish cotyledon. The reaction mixture contained 30 mM imidazole-nitrate buffer (pH 7.0), 0.1 mM menadione, and radish cotyledon, and was kept at 30° C. for 5 minutes. Open and closed symbols show the cotyledon after 5 days of incubation in the dark and after 10 days of incubation in the light, respectively.
Figure 5:
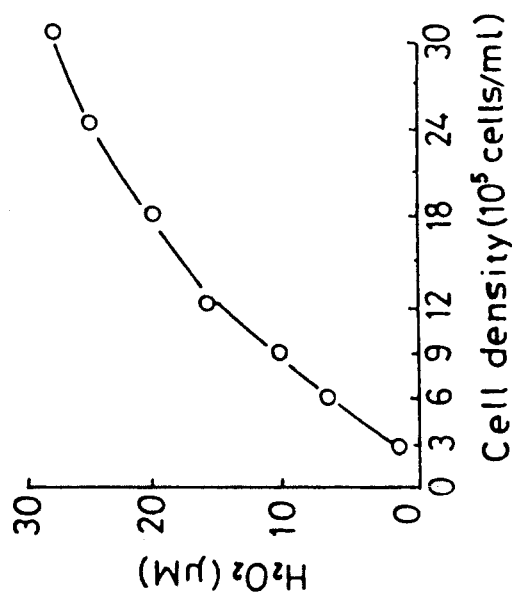
FIG. 5 shows a plot of $H_2O_2$ production vs. PC-3 cell density. The reaction mixture contained Hanks' medium, 0.1 mM menadione and PC-3 cells and was kept at 37° C. for 10 minutes.

We found the fact that quinone-catalyzed $H_2O_2$ production by intact cells and tissues is proportional to the cell density and tissues activity. We also observed that the rate of menadione-catalyzed $H_2O_2$ production was about 1/20 of that of menadione-catalyzed ferricyanide reduction and caused little consumption of intracellular NADH. This fact suggests that yeast cells have enough activity to supply NADH consumed by menadione-catalyzed $H_2O_2$ production. In fact, menadione-catalyzed $H_2O_2$ production was proportional to the cell density of yeast cells, but not to that of tumor cells. PC-3 cells showed no linear proportionality between cell density and $H_2O_2$ production at high concentrations of $H_2O_2$ produced in the medium, suggesting that PC-3 cells are sensitive to the toxic effect of $H_2O_2$. The assay for PC-3 cells should be performed under the condition that the concentration of $H_2O_2$ produced is below 20 $\mu$M, as shown in FIG. 5. The good correlation between $H_2O_2$ production and cotyledon wet weight was observed as shown in FIG. 6, but $H_2O_2$ production by cotyledon was less than that by yeast cells and PC-3 cells. For example, the rate of menadione-catalyzed $H_2O_2$ production by cotyledon was about 1/50 of that by yeast cells. Cells prepared from cotyledon may produce $H_2O_2$ more rapidly than cotyledon, because the surface of cells in contact with menadione is wider than that of intact cotyledon.

As mentioned above, the optimum conditions of the assay for each type of cells and tissues should be chosen to obtain the correlation between $H_2O_2$ production and cell density. Incubation time, quinone concentration, and temperature are the important factors of the assay in order to avoid the toxic effects of $H_2O_2$ and menadione. However, it will be understood that the chemiluminescent assay of the invention has merits such as simplicity and rapidity without the need for extraction of NAD(P)H, ATP, and other compounds from cells and tissues.

EXAMPLES

<Materials and Methods>

(1) Organisms and Growth Conditions

*Saccharomyces cerevisiae* strain IFO 2044 was grown aerobically at 30° C. in a medium containing 1% malt extract, 0.5% yeast extract, and 2% glucose (pH 5.8). The cells were harvested in the intial stationary phase of growth, washed twice, and suspended in 20 mM 4-(2-hydroxyethyl)-1-piperazineethanesulfonic acid (pH 7.0) or 30 mM imidazole-nitrate buffer (pH 7.0).

Radish seeds (*Raphanus sativus* L.) were germinated on wire screens over mineral water. Cotyledon and roots were harvested after 5 days of incubation at 27° C. in the dark or after 10 days of incubation in the light.

Prostate carcinoma cells, ATCC CRL-1435 (PC-3), were maintained in DME/F12 supplemented with 10% fetal bovine serum and were subcultured every 3 days from subconfluent plates. The cells were grown on Falcon tissue culture dishes in a humidified atmosphere of 95% air and 5% $CO_2$. Exponentially growing stock cells were trypsinized, and single cells thus obtained were collected by centrifugation and resuspended in serum-free medium.

The viable cell number was determined using 0.4% trypan blue stain and a hemocytometer.

(2) Determination of $H_2O_2$

One ml of the cell suspension or the medium containing plant tissue after incubation with menadione was introduced into the vial for the photomultiplier, and 1 ml of the solution containing 60 mg of TCPO and 10 mg of pyrene in 100 ml of acetonitrile was injected into the above vial through the tube. The chemiluminescence intensity after the injection was automatically counted for 5 seconds. A model ATP-237 Lumicounter (Tokyo Kagaku Sangyo) was used for the chemiluminescent assay.

<RESULTS>

(1) Determination of $H_2O_2$ Concentration

Figure 1:
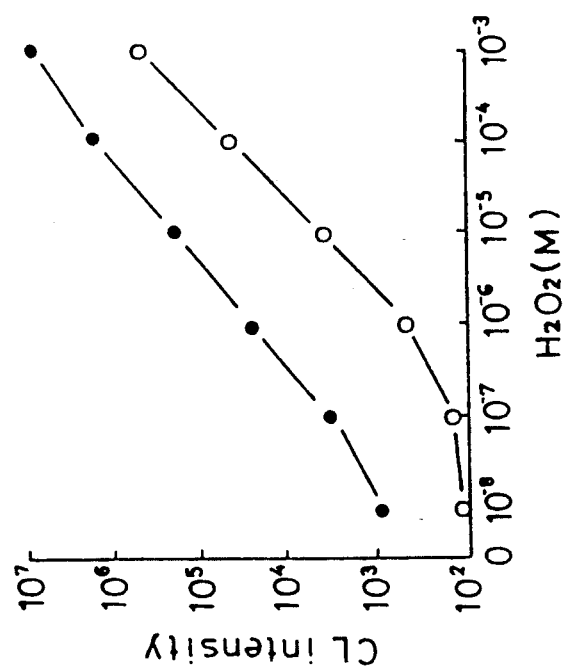
FIG. 1 shows a plot of the logarithm of chemiluminescence intensity (CL) vs. the logarithm of $H_2O_2$ concentration.

FIG. 1 shows a plot of the logarithm of chemiluminescence intensity vs. the logarithm of the concentration of $H_2O_2$. The chemiluminescence intensity was not affected by the serum, but was affected by halogen ions contained in the medium. For example, the chemiluminescence intensity in the medium containing 0.3% NaCl such as Earl's medium was about 1/100 of that in the NaCl-free medium, as shown in FIG. 1. Thus, it is necessary to check the effect of the medium containing halogen ions on the chemiluminescence intensity.

The direct mixing of TCPO solution and the cell suspension incubated with menadione did not affect the chemiluminescence intensity, but the acetonitrile in the TCPO solution caused the destruction of cells and tissues.

Figure 4:
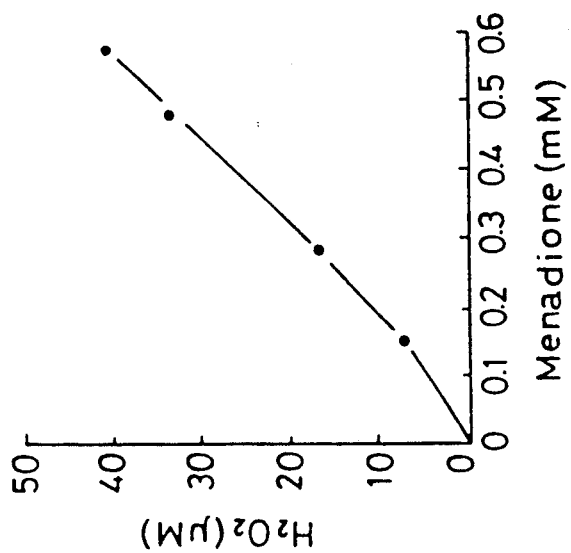
FIG. 4 shows the effect of menadione on $H_2O_2$ production by yeast cells. The reaction mixture contained 30 mM imidazole-nitrate buffer (pH 7.0) and yeast cells ($22 \times 10^7$ cells/ml), and was kept at 25° C. for 30 seconds.
Figure 3:
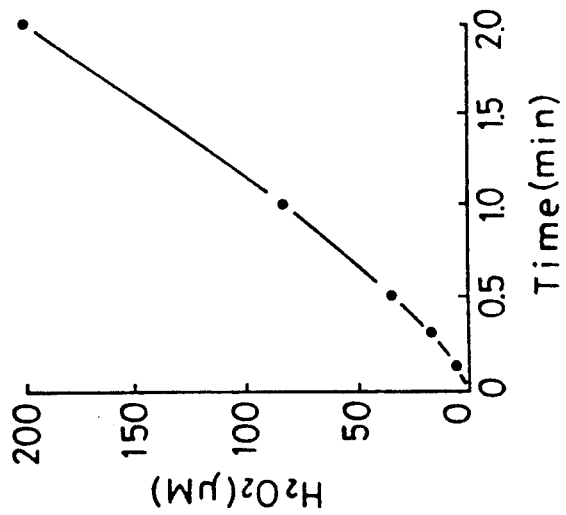
FIG. 3 shows the time course of $H_2O_2$ production by yeast cells. The reaction mixture contained 30 mM imidazole-nitrate buffer (pH 7.0), 0.5 mM menadione and yeast cells ($22 \times 10^7$ cells/ml), and was kept at 25° C.

(2) Assay for Yeast Cells $H_2O_2$ production was observed in the yeast cell suspension in the presence of menadione, but was not observed in the absence of menadione. When yeast cells were heated at 90° C. for 10 min., $H_2O_2$ production was not observed after addition of menadione. These facts show that $H_2O_2$ production catalyzed by menadione depends on cellular survival. FIG. 2 shows that $H_2O_2$ production is proportional to yeast cell density in the range from $10^4$ to $2.5 \times 10^5$ cells/ml. The chemiluminescence intensity at 0.1 $\mu$M $H_2O_2$ was about three times as large as that of the background signal, and it was sufficient to detect chemiluminescence intensity at $10^4$ cells/ml. The optimum menadione concentration and incubation time for the assay of yeast cells were 0.5 mM and 2 min., respectively. In addition, high cell density above $10^7$ cells/ml could be determined within 30 seconds without dilution of the cell suspension, as shown in FIG. 3. $H_2O_2$ production was promoted by menadione acting as the redox mediator and was proportional to the concentration of menadione, as shown in FIG. 4. The concentration of menadione used for the assay should be kept below 0.6 mM, because menadione had a toxic effect on cell growth. Thus, menadione should be used at lower concentrations for menadione-sensitive yeast cells.

When yeast cells were collected by centrifugation within 10 min. after the incubation of menadione, the supernatant could be used for determination of $H_2O_2$ concentration, and the collected cells showed the normal growth after being washed with water.

(3) Assay for Mammalian Cells

The cell density of PC-3 cells was proportional to the production of $H_2O_2$ in the presence of menadione, but this correlation was not linear, as shown in FIG. 5. $H_2O_2$ production by PC-3 cells slightly decreased with increasing cell density, suggesting that the $H_2O_2$ accumulated gives the oxidative stress to PC-3 cells to inhibit the production of $H_2O_2$. The detectable minimum cell density was $3 \times 10^5$ cells/ml under the conditions shown in FIG. 5. The concentration of menadione was kept at 0.1 mM, because PC-3 cells were sensitive to the toxic effect of menadione. The low cell density in the range from $10^4$ to $10^5$ cells/ml can be determined by using the simple mixture containing 0.25M sucrose, 5 mM imidazole nitrate buffer (pH 7.0), and 0.1 mM menadione. However, the medium containing various nutrients is useful in the assay system for determining many sample over the long term because of the maintenance of survival cells by uptake of nutrients. The incubation time shown in FIG. 5 is 5 min. and is much shorter than that in the colorimetric assay with MTT. The rapid change in cell activity is expected to be detected with the proposed assay.

(4) Assay for Plant Tissues $H_2O_2$ production by radish roots harvested after 10 days of incubation was below 1 nmol/20–40 mg wet wt., and there was no difference in $H_2O_2$ production between radish root grown in the dark and that grown in the light. The cotyledon of the radish grown in the dark for 5 days had the activity to produce about 1 nmol of $H_2O_2$/20-35 mg wet wt. for 5 min. under the conditions shown in FIG. 6 and showed no correlation between $H_2O_2$ production and cotyledon wet weight. Radish cotyledon harvested after 10 days of incubation in the light showed a linear correlation between $H_2O_2$ production and cotyledon wet weight as shown in FIG. 6. The calculated linear regression and correlation coefficient were $y=0.24 X-6.79$ and $r=0.79$, respectively.

This assay is expected to be useful for the determination of photosynthetic activity at various plant growth phases without destroying plant tissues. After radish incubated with menadione is removed from the medium, the medium can be used for the determination of $H_2O_2$, and radish can be used again for other analysis. Radish incubated with menadione for 10 min. showed normal growth after being washed with water.

What is claimed is:

1. A chemiluminescent assay for the determination of density or activity of viable cells which comprises:
    incubating viable cells containing an intracellular reductant in the presence of 2-methyl-1,4-naphthoquinone reducible by the intracellular reductant,
    reacting the 2-methyl-1,4-naphthoquinone with the intracellular reductant to produce 2-methyl-1,4-naphthoquinone in reduced form,
    reacting the reduced form of 2-methyl-1,4-naphthoquinone with dissolved oxygen to form hydrogen peroxide,
    reacting the hydrogen peroxide with a chemiluminescence reagent in the presence of a fluorescent substance having a pi electron to cause fluorescence, and
    determining density or activity of the cells on the basis of the intensity of fluorescence.

2. The assay of claim 1 in which the chemiluminescence reagent is bis(2,4-dinitrophenyl)oxalate or bis(2,4,6-trichlorophenyl)oxalate.

3. The assay of claim 1 in which the fluorescent substance is an aromatic compound having $\pi$-electrons.

4. The chemiluminescent assay of claim 3, wherein the fluorescent substance is pyrene or perylene.

5. The chemiluminescent assay of claim 1, wherein the intracellular reductant is a nicotinamide adenine nucleotide selected from the group consisting of NADH and NADPH.

* * * * *

UNITED STATES PATENT AND TRADEMARK OFFICE
CERTIFICATE OF CORRECTION

PATENT NO. : 5,093,238
DATED : March 3, 1992
INVENTOR(S) : Shiro Yamashoji et al It is certified that error appears in the above-indentified patent and that said Letters Patent is hereby corrected as shown below:

On the title page, Item [54] and Column 1, line 1, Change "DENSITY OF ACTIVITY" to -- DENSITY OR ACTIVITY --.

In line 4 of Abstract on face of patent: Change "redcues" to --reduces--.

Column 1, line 2: Change "DENSITY OF ACTIVITY" to --DENSITY OR ACTIVITY--.

Column 1, line 32: Change "Methods Vol." to --Methods vol.--. See Amendment dated 10/30/90, p. 2, 1. 1-2.

Column 1, line 32: Insert --)-- after "pp. 55-63".

Column 1, line 36: After "C", delete --.--.

Column 1, line 45: Change "Fla." to --FL--.

Column 1, line 48: Change "Fla." to --FL--.

Column 2, line 15: After "C", delete --.--.

Column 2, line 25: After "C", delete --.--.

Column 5, line 34: After "C", delete --.--.

Column 6, line 25: After "C", delete --.--.

UNITED STATES PATENT AND TRADEMARK OFFICE
CERTIFICATE OF CORRECTION

PATENT NO. : 5,093,238
DATED : March 3, 1992
INVENTOR(S) : Shiro Yamashoji et al It is certified that error appears in the above-indentified patent and that said Letters Patent is hereby corrected as shown below:

In figure entitled "Mechanism of Fluorescent Reaction" in columns 3 and 4: Add arrows as shown

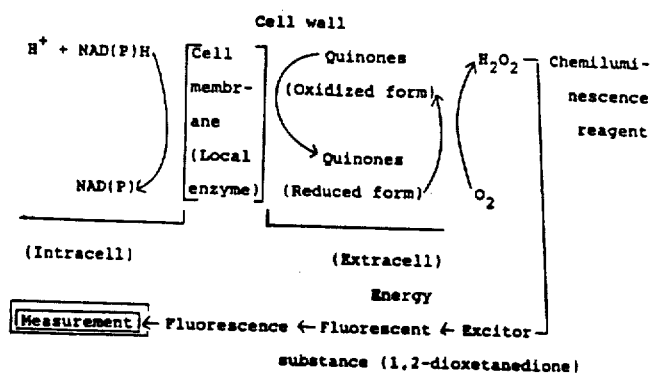

Signed and Sealed this

Fourteenth Day of September, 1993

Attest:

BRUCE LEHMAN

Attesting Officer     Commissioner of Patents and Trademarks